Figure 1:
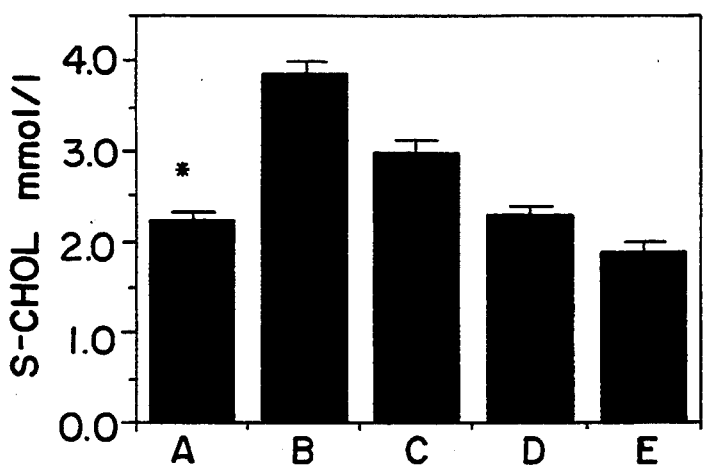

United States Patent [19]

Larsson-Backström

[11] Patent Number: 5,434,183

[45] Date of Patent: Jul. 18, 1995

[54] PHOSPHOLIPIDS CONTAINING OMEGA-3-FATTY ACIDS

[75] Inventor: Carin Larsson-Backström, Stockholm, Sweden

[73] Assignee: Pharmacia AB, Sweden

[21] Appl. No.: 157,024

[22] PCT Filed: May 19, 1992

[86] PCT No.: PCT/SE92/00333

§ 371 Date: Dec. 29, 1993

§ 102(e) Date: Dec. 29, 1993

[87] PCT Pub. No.: WO92/21335

PCT Pub. Date: Dec. 10, 1992

[30] Foreign Application Priority Data

May 30, 1991 [SE] Sweden ............................ 9101642

[51] Int. Cl.$^6$ ............................................. A61K 31/66
[52] U.S. Cl. ............................. 514/549; 514/552; 514/558; 514/560
[58] Field of Search ............... 514/549, 552, 558, 560

[56] References Cited

U.S. PATENT DOCUMENTS 4,820,731 4/1989 Mascioli et al. .................... 514/549

FOREIGN PATENT DOCUMENTS

| 333437 | 2/1974 | Austria. |
|---|---|---|
| 0304603A1 | 3/1989 | European Pat. Off.. |
| 3347269A1 | 7/1985 | Germany. |
| 3721137A1 | 1/1989 | Germany. |
| 8705122 | 6/1989 | Sweden. |
| WO86/00523 | 1/1986 | WIPO. |
| WO87/02247 | 4/1987 | WIPO. |

OTHER PUBLICATIONS

Production of Health Food Egg, JP 59-39258 (Abstract), vol. 8, No. 126 (C-228) (1984).
Carcinostatic Agent, JP 62-77319 (Abstract), vol. 11, No. 273 (C-445) (1987).
Love, et al., Specific accumulation of cholesterol–rich liposomes in the inflammatory tissue of rats with adjuvant arthritis, Annals of the Rheumatic Diseases, 1990, vol. 49, pp. 611–614.
Hamazaki, et al., Injection of Tridocosahexaenoyl–Glycerol Emulsion and Fatty Acid Composition of Blood Cells, Lipids, 1987, vol. 2(12), pp. 1031–1034.
Hamazaki, et al., The Infusion of Trieicosapentaenoyl–Glycerol into Humans and the In Vivo Formation of Prostaglandin I$_3$ and Thromboxane A$_3$, Biochem. Biophys. Res. Commun., 1988, vol. 151(3), pp. 1386–1394.
Billiar, et al., Fatty acid intake and Kupffer cell function: Fish oil alters eicosanoid and monokine production to endotoxin stimulation, Surgery, 1988, vol. 104(2), pp. 343–349.
Urakaze, et al., Infusion of Emulsified Trieicosapentaenoyl–Glycerol into Rabbits—The Effects of Platelet Aggregation, Polymorphonuclear Leukocyte Adhesion, and Fatty Acid Composition in Plasma and Platelet Phospholipids, Thrombosis Research, 1986, vol. 44, pp. 673–682.
Childs, et al., Divergent lipoprotein responses to fish oils with various ratios of eicosapentaenoic acid and docsahexaenoic acid[1-3], Am. J. Clin. Nutr., 1990, vol. 52, pp. 632–639.

Primary Examiner—Richard L. Raymond
Attorney, Agent, or Firm—Pollock, Vande Sande & Priddy

[57] ABSTRACT

The invention relates to an emulsion which comprises phospholipids containing omega-3-fatty acids such as DHA and EPA in a high amount and a vegetable oil and/or marine oil. It also relates to the use of phospholipids containing the omega-3-fatty acids such as DHA and EPA in high amount for the manufacturing of a nutritive emulsion giving low serum triglyceride and cholesterol levels and for the manufacturing of a medicament with anti-inflammatory and immunosuppressive effects. The invention also discloses phospholipids containing omega-3-fatty acids such as DHA and EPA with therapeutic effects such as effects on inflammatory and immunologically active cells, e.g. rheumatoid arthritis and sepsis and an effect on normal brain and retina development and function and cardiovascular diseases. Also disclosed are pharmaceutical and nutritive compositions as well as lipid particles comprising the phospholipids.

24 Claims, 3 Drawing Sheets

PHOSPHOLIPIDS CONTAINING OMEGA-3-FATTY ACIDS

This application is a 371 of PCT/SE92/00333, filed May 19, 1992.

Introduction

The present invention relates to emulsions containing phospholipids of marine and/or synthetic origin with a high mount of (at least 30% (w/w) of its total fatty acid content) omega-3 (hereinafter written as) w3-fatty acids, with docosahexaenoic acid, 22:6w3 (hereinafter written as DHA) and eicosapentaenoic acid, 20:5w3 (hereinafter written as EPA) in combination, as well as the use of these phospholipids. The phospholipids are used as emulsifiers, nutritive substrates, as a pharmacologically active agent in an emulsion, as a component in pharmaceutical compositions or as a component in lipid particles.

Background of the Invention

It is known that lipid emulsions can be used intravenously to constitute an energy dense caloric source and a source of essential fatty acids for those patients who have difficulties in using orally administered nutrition.

Since the beginning of the 1960s, fat emulsions which are intended for intravenous nutrient supply and which exhibit insignificant secondary effects have been available (Wretlind, A. Development of fat emulsions, JPEN 5: No 3,230–35, 1981).

This developmental work has investigated the effect of emulsions which contain a number of different fats, such as soy bean oil, maize oil, safflower oil, cottonseed oil etc. and different emulsifiers, such as soy bean phospholipids, egg yolk phospholipids etc.

Emulsions for nutritive or therapeutic use are, for example, described in U.S. Pat. No. 4,168,308.

The nutritive emulsions now most commonly used contain a vegetable oil such as soybean oil and/or safflower oil, an emulsifying agent such as an egg yolk phospholipid and water together with glycerol. An example of such an emulsion is Intralipid ®, manufactured since 1962 and sold by Kabi Pharmacia AB. Intralipid ® 10% contains 10% oil as soy bean oil and 1,2% egg yolk phospholipids.

Different fatty acids in the lipids have different physiological, biochemical and pharmacological properties and during the last years great interest has been concentrated on the importance of the w3-fatty acids, containing 18–22 carbon atoms.

The w3-fatty acids eicosapentaenoic acid (20:5w3, EPA) and docosahexaenoic acid (22:6w3, DHA) are essential fatty acids in man. Besides their nutritional value, they are also known to possess pharmacological effects. The most known and important are the cardiovascular effects, the beneficial effects on inflammatory and autoimmune diseases and the necessity of these fatty acids for the normal development of brain and retina functions.

These effects have such unimportance that a lot of work has been done to find good nutritional compositions containing a high mount of w3-fatty acids. See e.g. WO 87/02247 (Baxter) and U.S. Pat. No. 4,820,731 (New England Deaconess Hospital) in which marine oils are used which contain a high amount of the w3-fatty acids EPA and DHA.

The patient also needs omega-6 fatty acids (hereafter written as w6-fatty acids) which are found, for example, in vegetable oils. Nutrients given to patients should therefore also contain an appropriate vegetable oil. Infusion of lipid emulsions containing w6-fatty acids results, however, in a raised level of cholesterol and triglycerides in some patients, which should be avoided. Until now some patients depending on parenteral nutrition have not been able to avoid a certain increase of total cholesterol and triglycerides when an emulsion containing mainly w6-fatty acids is given. w6-Fatty acids also increase the level of eicosanoides and leucotrienes, which when overproduced in some patients, e.g. with overactive inflammatory and immunological reactions, may have deleterious effects.

Phospholipids containing EPA or DHA are known as being useful in various fields, such as foods, cosmetics, medicines, agriculture etc. and different methods for their-manufacture have been disclosed. See e.g. JP 2097393 and JP 1050890.

The use of phospholipids, containing EPA or DHA, as emulsifier for an EPA-triglyceride-emulsion and a DHA-triglyceride-emulsion, respectively, has been investigated by Hamazaki T et al in Biochem and Biophys Res Comm. Vol 151, No 3, 1386–1394, 1988; in LIPIDS Vol 22 No 12, 1031–1034, 1987 and in Thrombosis Research Vol 44, 1986, (673–682). Hamazaki found, for example, that both the EPA and DHA levels in platelets and RBC (red blood cell) membranes increased significantly when either the EPA or the DHA emulsion, respectively, were infused intravenously for a short time. Blood lipids remained unchanged, except for free fatty acids which decreased. Platelet aggregation and leucocyte adhesion were depressed mainly afar administration of the EPA containing emulsion.

The Swedish patent application SE 8705122-3 is related to a method for manufacturing fatty emulsions with phospholipids from eggs as an emulsifier consisting of at least 10% (w/w) w3-fatty acids, wherein the phospholipids are derived from eggs of animals fed with a diet rich in marine oils.

This method of incorporating w3-fatty acids in phospholipids is however provided with natural limitations. It has not been possible to exceed about 15% (w/w) of w3-fatty acids in phospholipids derived by this method, with the level of EPA about 2% (w/w), which in the conventional lipid emulsions described is to be considered to be below the level for therapeutic effects.

The egg phospholipids described in the above mentioned Swedish patent application does not necessarily have the therapeutic effects presumed.

Since there is evidence which suggests that dietary EPA can provide some clinical benefit in treatment of inflammatory diseases (Salmon, n-3 News, Vol II (3) 1987), it is important to have a high mount of DHA as well as EPA in the phospholipids.

DE 3347269 describes a method of how to synthetically manufacture lecithine and lyso-lecithine containing EPA and/or DHA, but does not reveal anything about the total amount incorporated of w3-fatty acids or the therpeutical use of the product.

No one has, however, investigated the biological effects and potency of phospholipids, and compared them with those of triglycerides, containing the w3-fatty acids such as EPA and DHA in combination in a high amount in an emulsion with an w6-fatty acid containing vegetable oil or the therapeutic use of phospholipids containing the w3-fatty acids such as EPA and DHA in combination in high amount

DESCRIPTION OF THE INVENTION

We have now found that when using the w3-fatty acids DHA and EPA in high amount in combination in phospholipids from marine or synthetic origin, instead of using them as triglycerides, but together with a vegetable oil containing w6-fatty acids in a nutritive lipid emulsion, the amount of serum cholesterol and triglycerides are surprisingly lower than with the same amount of w3-fatty acids given as fish oil. By using this origin of w3-fatty acids in phospholipids the amount of all the important w3-fatty acids, together with all the important and essential w6-fatty acids was increased in biological membranes. Furthermore, the incorporation of w3-fatty acids into biological membranes is unexpectedly increased.

It is also totally unexpected that the incorporation biological membranes of w3-fatty acids as well as w6-fatty acids is more efficient, and the potency is higher, by using the w3-fatty acid-rich phospholipid (according to the invention) than with the same amount of w3- and w6-fatty acids given as marine oil in emulsion or as vegetable oils in emulsion.

Most surprisingly and important is the finding that DHA is specifically increased in membrane phospholipids. This is of utmost importance since DHA, being the most important w3-fatty acid in phospholipids in biological membranes, does not compete with and decrease the level of arachidonic acid, the most important w6-fatty acid in phospholipids in biological membranes, as much as EPA does. In cholesterol esters also the level of EPA and alpha-linolenic acid are increased.

In all lipid fractions the level of arachidonic acid, which is the most important w6-fatty acid in biological membranes, is maintained constant. This is in contrary to the reduction of arachidonic acid in biological membranes, which is observed when using therapeutic doses of marine oils, containing a high amount of EPA. After the administration of fish phospholipids (according to the invention), however, even the levels in triglycerides of the w6-fatty acids are increased.

This indicates that the metabolism of arachidonic acid to eicosanoides is reduced and thus the w6-fatty acids are in good balance with the w3-fatty acids and are spared as important components in biological membranes.

The findings are of utmost interest for nutritive emulsions as the amount of total serum cholesterol and triglycerides should be kept as low as possible and the levels of w6- and w3-fatty acids in biological membranes should be kept in balance.

The findings are also of utmost interest to obtain normal and well balanced levels of essential fatty acids, w3-fatty acids as well as w6-fatty acids, for nutritive emulsions to premature/newborn babies and in long-term TPN (total parenteral nutrition). The specific increase in DHA in phospholipids together with the increase of all important w3- and w6-fatty acids in cholesterol esters and triglycerides fulfill the nutritive requirements of a well-balanced, increased level of W3-fatty acids as well as w6-fatty acids. Such emulsions can thus be useful nutritionally for example, in long term total parenteral nutrition (TPN) and in prematures/newborn patients, who need w3-fatty acids as well as w6-fatty acids for normal brain and retinal development.

Love et al, Annals of the Rheumatic Diseases, 1990, 49, pp 611–614 has shown that egg phospholipids are accumulated in immunologically active cells. Billiar T R et al ("Fatty add intake and Kupffer cell function; Fish oil alters eicosanoid and monokine production to endotoxin stimulation" Surgery, 104, 343–349 1988) has shown that w3-fatty acids are incorporated into and have anti-inflammatory effects on Kupffer cells, when fish oil with w3-fatty acids was given orally. We have now surprisingly found that w3-fatty acid containing marine phospholipids accumulate in Kupffer cells and that DHA from the marine phospholipids is incorporated in membrane phospholipids with an unexpectedly high specificity and potency. Also the other essential w3-fatty acids, EPA and alpha-linolenic acid, which are increased in cholesterol esters, as well as the essential w6-fatty acids are increased in neutral lipida. The increase in membrane lipids of w3-fatty acids as well as of w6-fatty acids show that the potency of the w3-fatty-adds is significantly higher after administration of w3-fatty acid containing marine phospholipids together with vegetable oil in emulsion (the invention) than after administration of comparable amounts of w3- and w6-fatty acids in fish oil and vegetable oil, respectively, in an emulsion.

The phospholipids according to the invention accumulate in Kupffer cells and can thus be used to reduce the w6-/w3-fatty acid ratio in stimulated immunologically active cells for the treatment of diseases with increased inflammatory and immunological reactions, e.g. sepsis, rhetmatoid arthritis or other autoimmune and inflammatory diseases.

The invention thus relates to an emulsion comprising vegetable oil and/or fish oil which contains phospholipid with the omega-3-fatty acids DHA and EPA in high amount in combination which can be used as a nutritive emulsion to meet the requirement of essential fatty acids, e. g. in long-term TPN and for premature/newborn babies. This emulsion can also be used for therapeutic purposes for a better w3-/w6-fatty acid balance, with serum lipid lowering and anti-inflammatory effects, effects on hemostatis, and in higher dosages immunosuppressive effects.

It also relates to the use of phospholipids containing w-3-fatty acids for the manufacturing of a medicament, with anti-inflammatory and immunosuppressive effects and the use of phospholipids with the omega 3-fatty acids DHA and EPA in combination for the manufacture of a nutrition emulsion giving low serum triglyceride and cholesterol levels and a more balanced w6-/w3-fatty acid ratio and with anti-inflammatory and immunosuppressive effects and effects on hemostatis:

The invention also relates to phospholipids containing the omega-3-fatty acids DHA and EPA with therapeutic effects on diseases with overproduction of eicosanoids in inflammatory and immunologically active cells, on rheumatoid arthritis, inflammatory situations and on the development and function of normal brain and retina. Another aspect of the invention is to use phospholipids with EPA and DHA in a high mount in combination with drugs with similar effects or used for diagnostic purposes.

The emulsion could comprise 0,5–40% (w/v of total emulsion) oil, preferably 5–30% (w/v), such as soybean oil, coconut oil, cottonseed oil, safflower oil, sunflower seed oil, linseed oil, borage oil, blackcurrent seed oil, canola oil, marine oil or a mixture of these. The mount of the phospholipids according to the invention could be 0,1–30% (w/v of total emulsion), preferably 0,1–10% (w/v). The phospholipids containing w3-fatty acids could be of marine or synthetic origin.

Other phospholipids such as egg yolk or soybean phospholipids and/or synthetic emulsifiers can also be included as complements in the emulsion. The total amount of emulsifier is preferably 0,1–30% (w/v of total emulsion).

The emulsion can also contain other components which normally are incorporated in emulsions e.g.: monoglycerides of fatty acids, components for adjusting of isotonic properties such as glycerol, anti-oxidants such as alpha-tocopherol, components for adjusting stability such as amino acids and carbohydrates such as fructose and glucose etc. It can also contain one or more bioactive compounds to be administered.

The preparation of the emulsion is carried out in a conventional manner. Thus the lipids are mixed with the aqueous phase, phospholipids according to the invention and optionally other emulsifiers and auxiliary agents in a suitable mixing device. The blend is thereafter homogenized to a desired particle size. The ways to adjust the emulsion to a suitable particle size is well known to a person skilled in the art.

Our findings are of utmost interest for nutritive emulsions to keep the amount of total cholesterol and triglycerides as low as possible for the patient and the balance of the ratio w6/w3-fatty acids in biological membranes optimal e. g. for newborn/premature infants, in long-term TPN and in situations with stimulated inflammatory and immunological reactions.

The phospholipids according to the invention are also concievable as components in lipid particles such as liposomes or any other mono-, bi- or multilayered vesicle.

The means and methods of how to use phospholipids to prepare such vesicles are well-known to anyone skilled in the art since numerous papers and patents have been published in this technical field (an overview of liposome preparation can be found in Drug Dev Ind Pharm 15 (19), 1523–54, 1989).

An aspect of the invention is to use the phospholipids with a high content of w3-fatty acids in the preparation of various lipid vesicles, either to deliver one or more bioactive components, or to be an administration form in itself for the highly therapeutically potent phospholipids.

Additional bioactive components can be enclosed in the vesicles or be parts of their membranes or can in certain cases be conjugated to the membrane molecules. These systems can be taylored individually for each bioactive molecule and depend on the net charge, molecular weight and the number of hydrophilic or hydrophobic groups on the molecules.

The bioactive compounds may be such that potentiates the therapeutical effects of the administered w3-fatty acids or any other drug, which is appropriate to deliver.

A bioactive Compound used in combination with the vesicles can also be a ligand with affinity to a biological receptor to create a more specific drug targeting system.

The vesicles may also be used for diagnostic purposes and the bioactive compound can in such cases be a labeled or signal-carrying molecule.

The vesicles prepared from the phospholipids according to the invention can be administered in conventional manners in pharmaceutical or diagnostical preparations. The additional ingredients for adapting the preparations for oral, buccal, parenteral, intraocular, nasal, pulmonary, rectal, or transdermal use are well-known for anyone skilled in the art.

The phospholipids according to the invention can also be administered in any oral, parenteral, intraocular, nasal, pulmonary, rectal or transdermal preparation in combination with conventional carriers and/or diluents. The administration forms can also, when appropriate comprise other adjuvants and enhancers for increasing or controlling membrane penetration such as monoglycerides and compounds with surface active properties.

FOLLOWING FIGURES ARE INCLUDED

FIG. 1 which shows the level of serum cholesterol (S-CHOL) after administration of different emulsions and solutions. See example 4.

Figure 2:
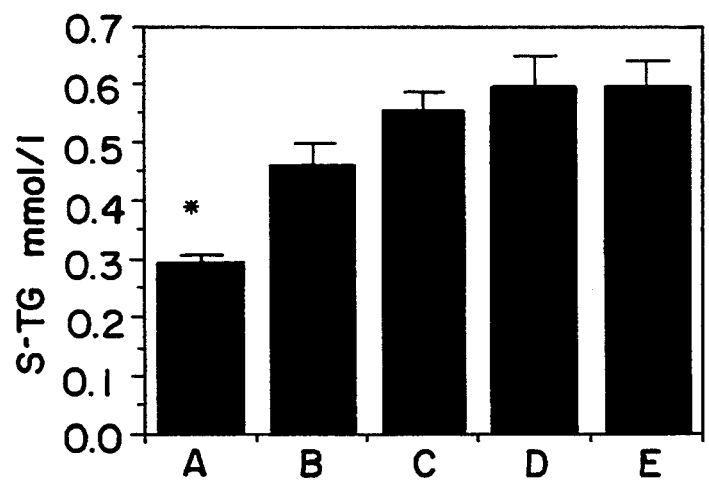

FIG. 2 which shows the level of serum triglycerides (S-TG) after administration of different emulsions and solutions. See example 4.

Figure 3:
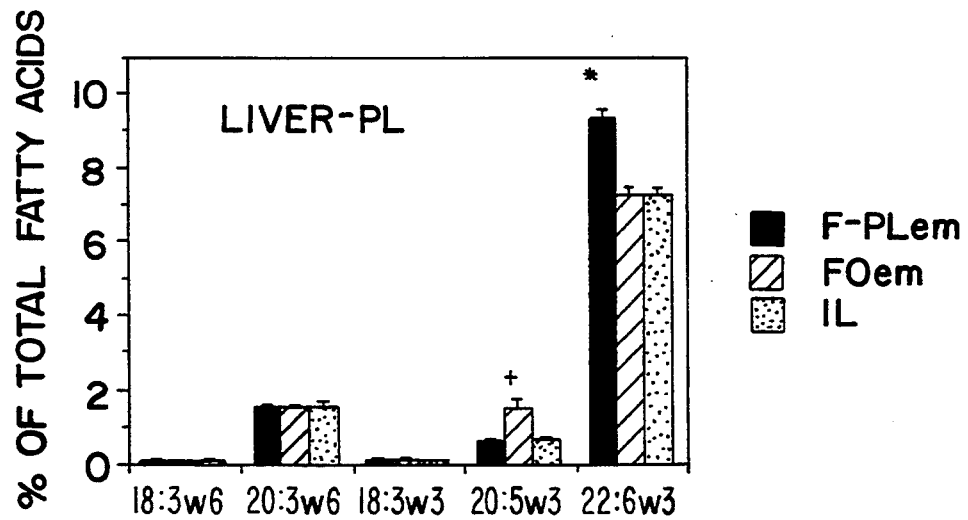
Figure 4:
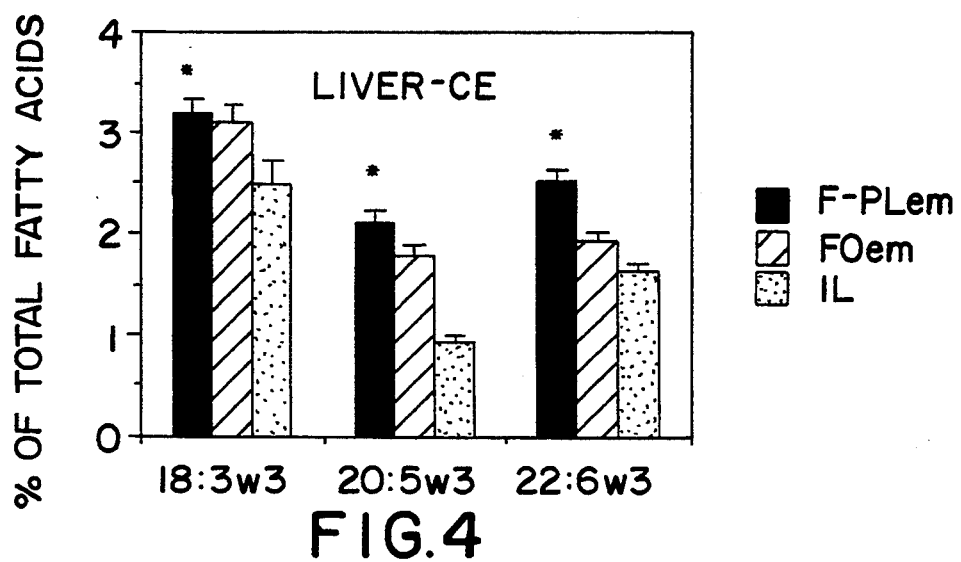
Figure 5:
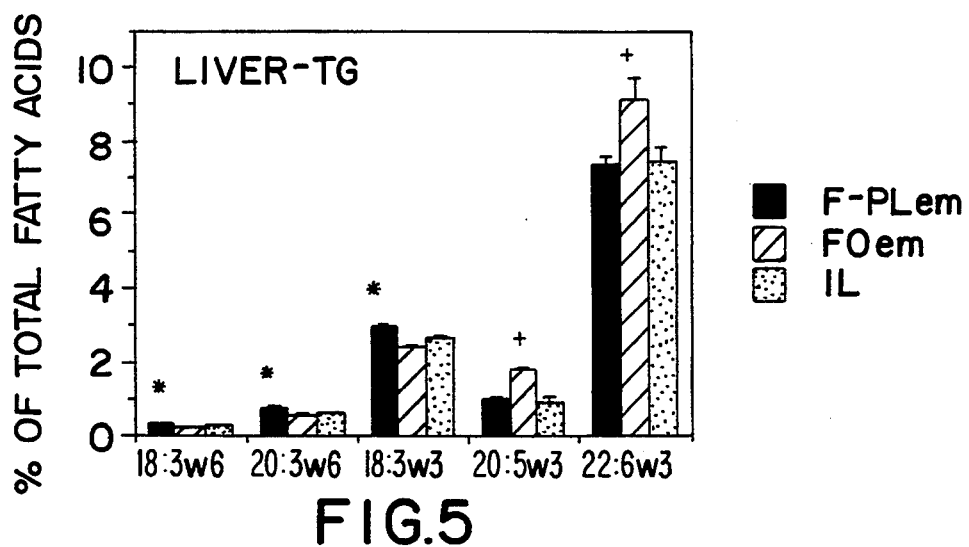

FIGS. 3–5 show the level in liver phospholipids (PL;FIG. 3), in liver cholesterol esters (CE; FIG. 4) and in liver triglycerides (TG; FIG. 5) of the most important w3-fatty acids DHA (22:6w3), EPA (20:5 w3), alphalinolenic acid (18:3 w3) and the w6-fatty acids dihomo-gamma-linolenic acid (20:3 w6) and gamma-linolenic acid (18:3 w6) after administration of different emulsions and solutions. See example 4. Statistically significant increase ($p < 0.05$, ANOVA) after administration of fish-phospholipid containing emulsion (*, F-PLem) compared to fish oil emulsion (FOem) and Intralipid (IL) and after FOem (+) compared to the other groups.

Figure 6:
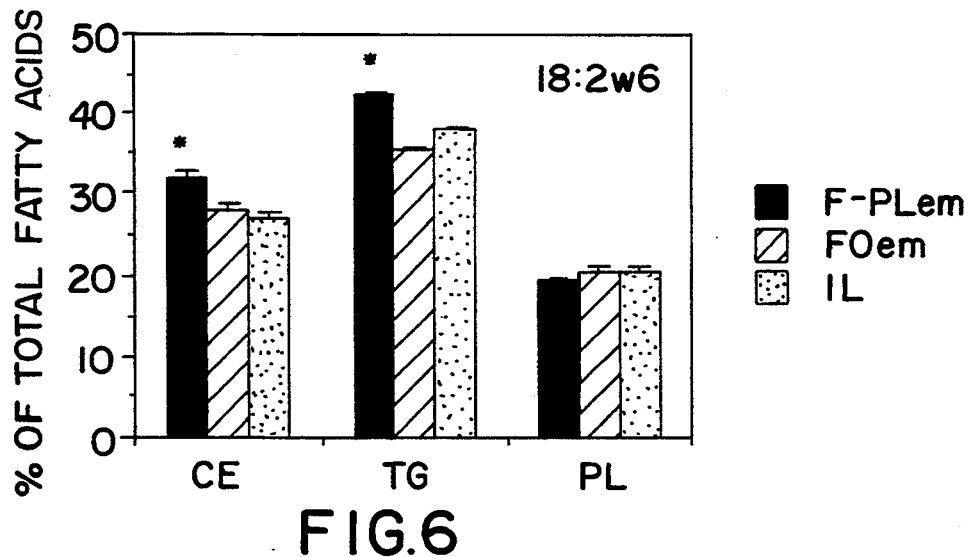

FIG. 6 shows the level of linoleic acid (18:2 w6) and

Figure 7:
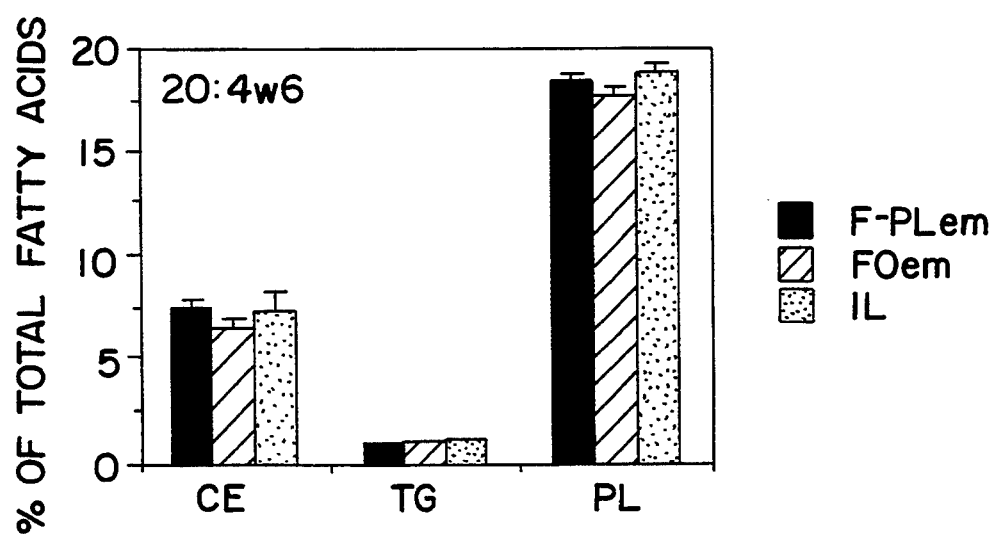

FIG. 7 shows the level of arachidonic acid (20:4 w6) in liver lipids after administration of different emulsions and solutions. See example 4. For explanation of abbreviations, see FIGS. 3–5.

Various modifications and equivalents of the emulsion will be apparent to one skilled in the art without departing from the spirit or scope of the invention. It is therefore to be understood that the invention is not to be limited to the specific examples and embodiments disclosed herein.

Fish phospholipids can be manufactured in different ways and in the following only one example of such a manufacturing is given.

EXAMPLES

Example 1

Preparation of fish phospholipids 1,5 kg fishmeal was extracted two consecutive times with 6 l and 3 l 95% ethanol. After filtration and pooling, ethanol was evaporated from the extract (vacuum, 40° C.). 134 g was left (22% of this was insoluble matter). This residue was dissolved in 1 volume petroleum ether, filtered, precipitated in four volumes −20° C. acetone, filtered and dissolved in petroleum ether. This last precipitation and dissolution was made twice. After precipitation again in four volumes of acetone, the solution was filtered and freeze-dried in a nitrogen atmosphere. The yield was 27 g.

The prepared fish phospholipid had the following fatty acid content in %:

| 14:0 | Myristic acid | 2 |
|------|---------------|----|
| 16:0 | Palmitic acid | 26 |

| 16:1 | Palmitoleic acid | 2,1 |
| 18:0 | Stearic acid | 3,0 |
| 18:1 | Oleic acid | 11,3 |
| 18:2 | Linoleic acid | 1,1 |
| 20:1 | Eicosenoic acid | 1,6 |
| 20:4 | Arachidonic acid | 1,2 |
| 20:5 | EPA | 10,6 |
| 22:6 | DHA | 32,4 |
| Total amount of fatty acids: 100% (w/w) | | |

Example 2

Preparation of a fish phospholipid emulsion according to the invention.

The fish phospholipid from example 1 was used for the manufacturing of an emulsion containing:

| 100 g | soybean oil |
| 12,0 g | fish phospholipid |
| 22,2 g | glycerol |
| 860 g | Aq. ad inject. |
| 3,0 ml | NaOH 1M |

The ingredients were mixed in a "Turrax-mixer" and thereafter homogenized in a "Moulin-Gaulin Homogenizer".

The soybean oil used had the following fatty acid content in %:

| 16:0 | Palmitic acid | 11 |
| 18:0 | Stearic acid | 4 |
| 18:1 | Oleic acid | 23 |
| 18:2 | Linoleic acid | 55 |
| 18:3 | Alfa-linolenic acid | 7 |
| Total amount of fatty acids: 100% (w/w) | | |

The total amount of w3-fatty acids is 12,2 g/l emulsion and the ratio w6-/w3-fatty acids is 4,5:1.

Example 3

Preparation of an emulsion contains fish oil and egg yolk phospholipids.

This emulsion was prepared according to the method described in Example 2, and contains a similar amount of w3-fatty acids and a similar w6/w3-fatty acid ratio as in Example 2.

The emulsion contained:

| Fish oil | 10,o g |
| Soy bean oil | 90,0 g |
| Egg yolk phospholipid | 12,0 g |
| Glycerol | 22,2 g |
| Aq. ad inject. | 860 g |
| NaOH, 1M | 3,0 ml |

As antioxidant vitamin E (alpha-tocopherol) was added to the emulsion The fish oil used had the following fatty acid content in %:

| 14:0 | Myristic acid | 6,3 |
| 16:0 | Palmitic aid | 14,7 |
| 16:1 | Palmitoleic acid | 7,3 |
| 18:0 | Stearic acid | 2,6 |
| 18:1 | Oleic acid | 8,9 |
| 18:1 | Vaccenic acid | 3,1 |
| 18:2 | Linoleic acid | 1,1 |
| 18:3 | Linolenic acid | 0,7 |
| 18:4 | Stearidonic acid | 2,6 |
| 20:1 | Eicosenoic acid | 1,5 |
| 20:4 | Arachidonic acid | 1,4 |
| 20:5 | EPA | 17,8 |
| 22:1 | Docosaenoic acid | 2,2 |
| 22:5 | Docosapentaenoic acid | 2,9 |
| 22:6 | DHA | 13,5 |
| Total amount of fatty acids: 100% (w/w). | | |

The egg yolk phospholipids used had the following fatty acid content in %:

| 14:0 | Myristic acid | 0,2 |
| 16:0 | Palmitic acid | 31,5 |
| 16:1 | Palmitoleic acid | 1,2 |
| 18:0 | Stearic acid | 14,1 |
| 18:1 | Oleic acid | 28,0 |
| 18:2 | Linoleic acid | 12,4 |
| 20:1 | Eicosenoic acid | 0,2 |
| 20:4 | Arachidonic acid | 4,2 |
| 22:6 | DHA | 5,8 |

The total mount of w3-fatty acids is 10,8 g/l emulsion and the ratio of w6-/w3-fatty acids is 4,8:1.

Example 4

Comparative example, (Fish phopholipid-fish oil)

The purpose of this example was to investigate the effects of the fish phospholipid preparation in an emulsion according to the invention and to compare it with different emulsions such as a fish oil emulsion containing the same amount of w3-fatty acids, Intralipid ® and also to compare it with fish phospholipids in water solution and physiological saline solution.

Male sprague Dawley rats, with weight on arrival of 170–190 g were used. The rats were placed individually in cages and provided with a preweighed small leather harness. The i.v. catheter was inserted 7–8 days later under anaesthesia. After the operation the animals were placed in the infusion room. Another 4 days were allowed for recovery.

After surgery the rats were provided with grounded laboratory stock diet R3 (Ewos AB; Södertälje, Sweden) and tap water ad libitum. During the entire test period the rats were provided with grounded laboratory stock diet R3 and tap water ad libitum.

The rats were randomized using a random unit into experimental groups A–E.

Six rats were used in each experimental group

All groups received 50 ml/kg body weight (b.w.)/day. Infusions were administrated intravenously via a permanent central vein catheter during 20 h/day, normally from 1 p.m. to 9 a.m., via IMED volumetric pumps.

Food consumption was recorded on a 24 h basis. The general appearance of the rats was recorded. The infusions were given during 9 consecutive. days. On day 10 the infusions were stopped at 7.00 a.m. and the oral food withdrawn.

The groups A–E were given the following infusions:
A: 10% Fat emulsion according to Example 2 (F-PLem, the Invention)
B: -"- according to Example 3 (FOem)
C: 10% Intralipid ®, containing 10% (w/v) oil as soy bean oil and 1,2% egg yolk phospholipid
D: 1.2% Phospholipid Solution containing:

| Fish phospholipids | 12,0 g |

-continued

| | |
|---|---|
| Glycerol | 22,2 g |
| Aq. ad inject. | 967 g |
| NaOH 1M | 3 ml |

E: 0.9% NaCl-solution

The amount of w3- and w6-fatty acids were as follows:

| | tot w3-FA | g/l tot w6-FA | w6/w3 |
|---|---|---|---|
| A = Ex 2 (Invention) | 12,2 | 55,2 | 4,5 |
| B = Ex 3 (Fish oil) | 10,8 | 51,6 | 4,8 |
| C = Intralipid | 7,7 | 56,8 | 7,4 |
| D = Fish phospholipid solution | 4,8 | 0,3 | 0,1 |

Approx. 2 hours after stopping the infusions, the rats were anaesthetized with Mebumal ® (60 mg/kg). The blood samples were collected for analysis of serum lipids.

Serum lipids: From 1 ml blood, serum was taken for analysis of serum triglycerides and serum cholesterol and frozen at −70° C. until analysis. Serum cholesterol was measured enzymatically. Serum triglycerides were measured enzymatically after eliminating free glycerol and enzymatic hydrolysis.

Histopathology; liver, kidneys, heart, lungs, spleen and thymus were excised, weighed and prepared for histopathological examination by embedding in paraffin and sectioning at 4-5 micrometer, then staining with haematoxylin-eosin. Frozen sections from all the tissues stained with Oil Red O for fat were also examined.

Fatty acid profile in liver lipids. The remaining liver tissue from rats in Groups A-C was used for measurement of fatty acid profile in neutral lipids and phospholipids(PL). The neutral lipid fractions examined were cholesterol esters (CE) and triglycerides (TG). The lipid material was extracted and the fatty acids derivatized and analyzed (GLC) using conventional methods.

The resulting data on serum lipids are shown in FIG. 1 (level of serum cholesterol, S-CHOL) and FIG. 2 (level of serum triglycerides, S-TG). The levels of the most important fatty acids in liver lipids are shown in FIGS. 3-7. The results are expressed as mean values ±SEM for the different emulsions and solutions.

Results and conclusions

FIG. 1 clearly shows that the serum cholesterol level is very low when the emulsion according to the invention is used (*A<B, C; p<0.05, ANOVA). The most surprising effect, however, is the result when comparing the serum triglyceride levels. See FIG. 2. That level is surprisingly low (0,30 mmol/l) and only half of the value when Intralipid ®, fish phospholipids in a solution or NaCl solution (0,60 mmol/l) were used (*A<B, C, D, E; p<0.05, ANOVA).

It is absolutely unexpected and unknown, that the small amount of w3-fatty adds which can be derived from phospholipids in a lipid emulsion, can exert physiological effects. The same amount of w3-fatty acids in triglycerides (Group B) does not exert the same biological effects or effects on fatty acid incorporation. Since the phospholipid/triglyceride ratio is about 1:10 in a 10% lipid emulsion and 1:20 in a 20% lipid emulsion, and the threshold level for biological effects for fish oil, containing about 30% w3-fatty acids, is at least 10% of the oil phase, the amount of w3-fatty acids in the phospholipid part of a lipid emulsion should be at least 30% (w/w of total fatty acids) to be expected to exert biological effects.

Thus giving an emulsion, according to the invention allows the patient to receive all essential fatty acids such as w6- and w3-fatty acids and still remain at a very low level of serum cholesterol and serum triglycerides.

The histopathological data showed that the emulsions with fish oil or fish phospholipids were accumulated mainly in the Kupffer cells in the liver, whereas Intralipid ® was accumulated as well in hepatocytes. Fish phospholipids in water solution were however accumulated only in Kupffer cells in the liver and in similar cells in the spleen. These cells are immunologically active. This specific accumulation to immunologically active cells facilitates an effect of w3-fatty acids on inflammatory and immunological reactions. This is of importance when using fish phospholipids for inflammatory or immunological diseases such as rheumateid arthritis and sepsis (Love et al., 1990 and Billiar et al.,1988) or to reduce the incidence of arterosderosis.

The fatty acid pattern in liver phospholipids and liver cholesterol esters show that EPA and DHA are incorporated better after treatment with the emulsion according to the invention when compared to the fish oil emulsion containing the same amount of w3-fatty acids.

The changes induced by fish phospholipid containing emulsion (F-PLem), fish oil containing emulsion (FOem) or Intralipid (IL) in fatty acid pattern in liver phospholipids (PL), cholesterol esters (CE) and triglycerides (TG) are shown in FIGS. 3-7. In the phospholipid fraction (FIGS. 3 and 6), the only changes seen were increases in DHA, induced by F-PLem (invention, *) p<0.05, ANOVA) and in EPA, induced by FOem (+p<0.05, ANOVA).

The specific increase in DHA in phospholipids, the main pool for DHA, is of importance for brain and retina development.

The uptake of and the level in biological membranes of polyunsaturated fatty acids, especially DHA in brain, is well correlated with that in liver (Anderson and Connor,Lipids 1988, 23(4), 286–290) and in heart (Swanson et al., British Journal of Nutrition, 1988, 59, 535–545). Thus a similar enhancement of uptake in brain and heart is expected following administration of the invented emulsion compared to the fish oil emulsion. Therefore the invented emulsion can be used also for normal brain and retina development and for cardiovascular diseases.

In the liver cholesterol ester fraction (FIGS. 4 and 6) F-PLem increased DHA, EPA and linoleic acid (18:2w6), compared to the FOem- and the IL-groups, and α-linolenic acid (18:3w3), compared to the IL-group. Thus, w3-fatty acids administered in the phospholipid form, are more effectively incorporated in membrane lipids (phospholipids and cholesterol esters) than w3-fatty acids in the glyceride form (fish oil) are. The main functions of the essential fatty acids are thus also the w3-fatty acids are exerted in the membrane lipids.

No decrease in any of the w6-fatty acids could be seen in the F-PLem group. On the contrary, the w6-fatty acids linoleic acid (18:2 w6, FIG. 6), gamma-linolenic acid (18:3w6) and dihomo-gamma-linolenic acid (20:3w6), as well as alpha-linolenic acid (18:3w3) (FIG. 5) were increased in the triglyceride fraction, compared to the FOem- and IL-groups. The level of arachidonic acid (20:4w6) remained unchanged in all lipid fractions (FIG. 7). This finding is of significance because of the importance of arachidonic acid in biological membranes.

Since the w3-fatty acid containing phospholipids are taken up more in Kupffer cells than in hepatocytes, as shown in the invention, the relative increase in incorporated w3-fatty acids is expected to be even higher in immunologically active cells (Kupffer cells and other macrophages) than in the whole liver. This is of importance for the anti-inflammatory and immunosuppressive effects exerted by the w3-fatty acids. The biological effects obtained by the w3-fatty acids in phospholipids can be used for therapeutic purposes as such or in combination with drugs with similar effects and included in the phospholipid vesicles (liposomes).

Conclusions

We have shown that marine phospholipids in an emulsion according to the invention result in surprisingly lower serum triglyceride and serum cholesterol levels when compared to fish oil emulsion, containing a similar amount of w3-fatty acids and a similar w6/w3-fatty acids ratio. Marine phospholipids induce more effective incorporation of w3-fatty acids in biological membranes than fish oil, containing a comparable amount of w3-fatty acids, in an emulsion.

These results show that a very favorable fatty acid pattern in membrane lipids is obtained, with an increase in all important w3-fatty acids as well as in the w6-fatty acids linoleic, gamma-linolenic and dihomo-gamma-linolenic acids. The invented w3-fatty acid containing phospholipid is therefore important in all situations with increased need of all essential fatty acids, since it makes it possible to increase the w3-fatty acids (from the invented phospholipid) as well as the w6-fatty acids (in vegetable oils) in a well-balanced pattern.

These results have implications for the use of w3-fatty acid containing phospholipids in vegetable oil emulsions for a more effective utilization and incorporation of w3- and w6-fatty acids. The use of w3-fatty acid containing phospholipids also allows a more specific incorporation of w3fatty acids in immunologically active cells.

The invention may have implications specifically for situations with increased level of serum lipids, increased inflammatory response and increased immunological activity and also for the normal development of the brain and retina.

The biological effects obtained by the w3-fatty acids in phospholipids can be used for therapeutic purposes as such or in combination with drugs with similar effects and included in the phospholipid vesicles (liposomes).

I claim:

1. An emulsion comprising vegetable oil and/or marine oil, an aqueous phase and phospholipids as emulsifier characterized in that the phospholipids are of marine and/or synthetic origin and contain omega-3-fatty acids in an amount of at least 30% (w/w).

2. The emulsion of claim 1 which comprises a vegetable oil.

3. An emulsion according to claim 1 characterized in that the omega-3-fatty acids, present in an amount of at least 30% (w/w), are DHA and EPA.

4. An emulsion according to claim 3 characterized in that the amount of oil is 0,5–40% (w/v) and the amount of phospholipids containing the omega-3-fatty acids is 0,1–20% (w/v).

5. An emulsion according to claim 1 characterized in that the amount of oil is 0.5–40% (w/v) and the amount of phospholipids containing the omega-3-fatty acids is 0.1–30% (w/v).

6. An emulsion according to claim 5 characterized in that it contains one or more bioactive compounds.

7. Phospholipids of marine and/or synthetic origin containing omega-3-fatty acids in an amount of at least 30% (w/w) with therapeutic effect.

8. Phospholipids according to claim 7 characterized in that omega-3-fatty acids are DHA and EPA in an amount of at least 30% (w/w).

9. A mono-, bi and/or multilayered vesicle or any mixture thereof characterized by its content of phospholipids containing the omega 3-fatty acids in an mount of more than 30% (w/w).

10. A mono-, bi and/or multilayered vesicle or any mixture thereof according to claim 9 characterized in that the omega 3-fatty acids are EPA and DHA.

11. A composition comprising the vesicles according to claim 9, campers and/or diluents and optionally one or more bioactive compound(s) combined with the vesicles.

12. A composition comprising the vesicles according to claim 10, carriers and/or diluents and optionally one or more bioactive compound(s) combined with the vesicles.

13. A pharmaceutical composition comprising the phospholipids according to claim 7 and carriers and/or diluents for adapting it to oral, nasal, pulmonary, rectal, ocular, transdermal or parenteral administration optionally in combination with one or more bioactive compound(s).

14. The pharmaceutical composition of claim 13 wherein the phospholipid is in an amount sufficient for anti-inflammatory and/or immunosuppressive effects.

15. A pharmaceutical composition comprising the phospholipids according to claim 8 and carriers and/or diluents for adapting it to oral, nasal, pulmonary, rectal, ocular, transdermal or parenteral administration optionally in combination with one or more bioactive compound(s).

16. A nutritive composition comprising the phospholipids according to claim 7 and carriers and/or diluents.

17. The nutritive composition of claim 16 being capable of giving low blood triglyceride and cholesterol levels.

18. A nutritive composition comprising the phospolipids according to claim 8 and carriers and/or diluents.

19. A method for treating a patient in need of anti-inflammatory and/or immunosuppressive effects which comprises administering to said patient an effective amount of the phospholipids of claim 7.

20. A method for treating a patient in need of anti-inflammatory and/or immunosuppressive effects which comprises administering to said patient an effective amount of the phospholipids of claim 8.

21. A method for treating a patient suffering from rheumatoid arthritis or sepsis which comprises administering to said patient an effective amount of the phospholipids of claim 7.

22. A method for treating a patient suffering from rheumatoid arthritis or sepsis which comprises administering to said patient an effective amount of the phospholipids of claim 8.

23. A method for promoting normal brain and/or retina development and function in a patient which comprises administering to said patient an effective amount of the phospholipids of claim 7.

24. A method for promoting normal brain and/or retina development and function in a patient which comprises administering to said patient an effective amount of the phospholipids of claim 8.

* * * * *